US009474495B2

(12) United States Patent
Ahn et al.

(10) Patent No.: US 9,474,495 B2
(45) Date of Patent: Oct. 25, 2016

(54) SYSTEM AND METHOD FOR JOINT ESTIMATION OF ATTENUATION AND ACTIVITY INFORMATION

(71) Applicant: General Electric Company, Schenectady, NY (US)

(72) Inventors: Sangtae Ahn, Guilderland, NY (US); Ravindra Mohan Manjeshwar, Glenville, NY (US); Florian Wiesinger, Garching (DE); Dattesh Dayanand Shanbhag, Bangalore (IN); Sandeep Suryanarayana Kaushik, Bangalore (IN); Hua Qian, Niskayuna, NY (US); Anne Menini, Garching (DE)

(73) Assignee: General Electric Company, Niskayuna, NY (US)

( * ) Notice: Subject to any disclaimer, the term of this patent is extended or adjusted under 35 U.S.C. 154(b) by 142 days.

(21) Appl. No.: 14/579,039

(22) Filed: Dec. 22, 2014

(65) Prior Publication Data

US 2016/0174919 A1  Jun. 23, 2016

(51) Int. Cl.
*A61B 6/00* (2006.01)
*G06T 7/00* (2006.01)
(Continued)

(52) U.S. Cl.
CPC ........... *A61B 6/4417* (2013.01); *A61B 5/0059* (2013.01); *A61B 5/055* (2013.01);
(Continued)

(58) Field of Classification Search
CPC . G06T 7/0012; G06T 7/0024; G06T 7/0034; G06T 11/003; G06T 11/005; G06T 11/008; G06T 2207/10072; G06T 2207/10081; G06T 2207/10084; G06T 2207/10088; G06T 2207/10104; G06T 2207/10108; G06T 2207/20076; G06T 2207/20212; G06T 2207/20221; G06T 2211/40; A61B 6/032; A61B 6/037; A61B 6/4417; A61B 6/5229; A61B 6/5235; A61B 6/5247; A61B 6/5258; A61B 8/4416; A61B 8/5238; A61B 8/5261; A61B 8/5269
See application file for complete search history.

(56) References Cited

U.S. PATENT DOCUMENTS

2006/0215891 A1  9/2006  Fessler et al. ................. 382/128
2011/0158497 A1  6/2011  Schweizer et al. ........... 382/131
(Continued)

FOREIGN PATENT DOCUMENTS

WO       2014074148 A1    5/2014

OTHER PUBLICATIONS

Fei et al., "MR/PET Quantification Tools: Registration, Segmentation, Classification, and MR-Based Attenuation Correction", Medical Physics, vol. 39, Issue 10, pp. 6443-6454, Oct. 2012.
(Continued)

*Primary Examiner* — Andrew W Johns
(74) *Attorney, Agent, or Firm* — Melissa K. Dobson

(57) ABSTRACT

Imaging system and method are presented. Emission scan (ES) and anatomical scan (AS) data corresponding to a target volume in a subject are received. One or more at least partial AS images are reconstructed using AS data. An image-space certainty (IC) map representing a confidence level (CL) for attenuation coefficients of selected voxels in AS images and a preliminary attenuation (PA) map based on AS images are generated. One or more of selected attenuation factors (AF) in projection-space are initialized based on PA map. A projection-space certainty (PC) map representing CL for the selected AF is generated based on IC map. An emission image of the target volume is initialized. The selected AF and emission image are iteratively updated based on the ES data, PC map, initial AF, and/or initial emission image. A desired emission image and/or AF values are determined based on the iteratively updated AF and/or emission image.

20 Claims, 6 Drawing Sheets

(51) Int. Cl.

| | | |
|---|---|---|
| *G01R 33/56* | (2006.01) | |
| *G01T 1/24* | (2006.01) | |
| *G06T 11/00* | (2006.01) | |
| *A61B 6/03* | (2006.01) | |
| *A61B 5/055* | (2006.01) | |
| *A61B 5/00* | (2006.01) | |
| *A61B 5/053* | (2006.01) | |
| *A61B 8/00* | (2006.01) | |

(52) U.S. Cl.
CPC .......... *A61B 5/0536* (2013.01); *A61B 6/032* (2013.01); *A61B 6/037* (2013.01); *A61B 8/4416* (2013.01); *G01R 33/56* (2013.01); *G01T 1/249* (2013.01); *G06T 7/0012* (2013.01); *G06T 7/0024* (2013.01); *G06T 7/0081* (2013.01); *G06T 11/003* (2013.01); *G06T 2200/04* (2013.01); *G06T 2207/10081* (2013.01); *G06T 2207/10088* (2013.01); *G06T 2207/10104* (2013.01); *G06T 2207/30024* (2013.01); *G06T 2207/30061* (2013.01); *G06T 2211/40* (2013.01)

(56) References Cited

U.S. PATENT DOCUMENTS

2013/0243298 A1* 9/2013 Bredno et al. ............ G06T 5/50
 382/131
2013/0248719 A1 9/2013 Volokh et al. ................ 250/362
2014/0056500 A1 2/2014 Bal et al. .............. G06T 11/005

OTHER PUBLICATIONS

Panin et al., "Reconstruction of uniform sensitivity emission image with partially known axial attenuation information in PET-CT scanners", 2012 IEEE Nuclear Science Symposium and Medical Imaging Conference Record, pp. 2166-2173, Oct.-Nov. 2012.
Rezaei et al., "Simultaneous Reconstruction of Activity and Attenuation in Time-of-Flight PET", IEEE Transactions on Medical Imaging, vol. 31, Issue 12, pp. 2224-2233, Dec. 2012.
Ahn et al., "Improved Attenuation Correction in PET/MRI by Combining MR Image Segmentation and Joint Estimation Approaches", The Journal of Nuclear Medicine, vol. 54, Issue 2, Abstract—2 Pages, 2013.
Rezaei et al., "ML-Reconstruction for TOF-PET With Simultaneous Estimation of the Attenuation Factors", IEEE Trans Medical Imaging, vol. 33, Issue 7, pp. 1563-1572, Jul. 2014.

* cited by examiner

SYSTEM AND METHOD FOR JOINT ESTIMATION OF ATTENUATION AND ACTIVITY INFORMATION

BACKGROUND

Embodiments of the present specification relate generally to diagnostic imaging, and more particularly to methods and systems for joint estimation of attenuation and activity information.

Positron emission tomography (PET) finds use in generating images that represent a distribution of positron-emitting nuclides, for example, within a patient's body. Accordingly, during PET imaging, a radionuclide is injected into the patient. As the radionuclide decays, positrons are emitted that collide with electrons, thereby resulting in an annihilation event. The annihilation converts the entire mass of the positron-electron pair into two 511 kilo-electron volt (keV) photons emitted in substantially opposite directions along a line of response (LOR). The PET system includes one or more detectors that are placed along the LOR on a detector ring to detect the annihilation photons. Particularly, the detectors detect a coincidence event if the photons arrive and are detected at the detector elements within a coincidence time window. Subsequently, the PET system uses the detected coincidence information along with other acquired image data for ascertaining localized concentrations of the radionuclide for use in generating a functional diagnostic image.

However, during imaging, the photon-electron interactions may result in attenuation of emitted photons, which in turn, may lead to inaccurate PET quantitation and/or degraded image quality. Accordingly, certain PET imaging approaches are drawn to joint estimation of PET attenuation and activity or emission maps from PET emission scan data, where all voxels/pixels are initially unknown. However, the conventional joint estimation approaches may result in cross-talk artifacts and incorrect scaling due to an under-determinedness and ill-conditionedness of the corresponding inverse problem, thus leading to incorrect PET attenuation correction.

Accordingly, PET imaging is often combined with an external radioactive source to measure attenuation factors in projection-space or to reconstruct an attenuation map in image-space that is representative of a spatial distribution of linear attenuation coefficients for the emission photons. Alternatively, an attenuation map is obtained from anatomical scan data acquired using an anatomical imaging scanner. For example, in conventional emission tomography systems, PET imaging may be combined with computed tomography (CT) or magnetic resonance imaging (MRI) to correct for the photon attenuations.

Although CT may produce anatomical transmission data of desired statistical quality, CT imaging provides limited soft-tissue contrast and involves administering substantial radiation to a patient. Accordingly, in certain imaging scenarios, MRI may be used in conjunction with PET imaging for generating high-quality images for use in providing efficient diagnosis and/or treatment to a patient. To that end, MRI and PET scans may be performed sequentially in separate scanners or simultaneously in a combined PET/MRI scanner. Particularly, simultaneous acquisition of PET and MRI data provides unique opportunities to study biochemical processes through fusion of complementary information determined using the orthogonal MRI and PET imaging modalities.

MRI, however, may not provide a direct transformation of magnetic resonance (MR) images into PET attenuation values. Generally, the MR images reflect distribution of hydrogen nuclei with relaxation properties rather than electron density, which is related to PET attenuation. Accordingly, certain conventional imaging approaches employ segmentation or atlas-based registration of the MR images to produce a corresponding patient-specific attenuation map. The attenuation map is then forward-projected to determine attenuation factors, which in turn, are used to reconstruct corresponding PET activity or emission images. Use of MRI information, thus, enhances PET attenuation correction and the subsequent PET image reconstruction.

However, the MRI information provides insufficient distinction between regions including lungs, air, bone, and/or metal even though these constituent materials have substantially different PET attenuation values. Accordingly, use of conventional segmentation and/or atlas-based approaches for estimation of PET attenuation maps using MRI information may result in inaccurate attenuation correction, particularly in and/or near metal, bones, and lungs, subsequently leading to PET activity quantitation errors. Particularly, the atlas-based approaches may be unable to address significant inter-patient variations in anatomy particularly for patient body parts other than heads. Moreover, in certain scenarios, MRI may provide only a truncated field of view (FOV) and may not suitably account for presence of extra-patient components such as beds and coils in the vicinity. The truncated FOV and the extra-patient components may also contribute to photon attenuation, in turn, leading to inaccurate PET quantitation and/or degraded image quality.

Accordingly, there is a need for a method and a system that mitigate the shortcomings of these conventional approaches to provide accurate attenuation correction in emission scan data. Particularly, it would be desirable to design a method and a system that address insufficiency and/or inaccuracy of MR-based attenuation images to provide efficient estimation of the attenuation values in and/or near conventionally unclassifiable regions such as metal, air pockets, bones, and lungs, thereby allowing for accurate PET quantitation and image reconstruction.

BRIEF DESCRIPTION

In accordance with one aspect of the present specification, a method, a system, and a non-transitory computer readable medium that stores instructions executable by one or more processors to perform a method for imaging a subject is presented. The method includes receiving emission scan data and anatomical scan data corresponding to the target volume in the subject. Further, the method includes reconstructing one or more at least partial anatomical scan images using the anatomical scan data. Additionally, the method includes generating an image-space certainty map that represents a level of confidence corresponding to an attenuation coefficient for one or more selected voxels in the one or more at least partial anatomical scan images. Moreover, the method includes generating a preliminary attenuation map based on the one or more at least partial anatomical scan images. Further, the method includes initializing one or more of a selected set of attenuation factors in a projection-space corresponding to the emission scan data based on the preliminary attenuation map. Additionally, the method includes generating a projection-space certainty map corresponding to the emission scan data that represents a level of confidence corresponding to a value of one or more of the selected set of attenuation factors based on the image-space certainty map. The method also includes initializing an emission image corresponding to the target volume. Furthermore, the method includes iteratively updating one or more of the selected attenuation factors and the emission image based on the emission scan data, the projection-space certainty map, the initial attenuation factors, and/or the initial emission image. Moreover, the method includes determining a desired emission image and/or desired values of the attenuation factors based on the iteratively updated attenuation factors and the iteratively updated emission image.

DRAWINGS

These and other features and aspects of embodiments of the present technique will become better understood when the following detailed description is read with reference to the accompanying drawings in which like characters represent like parts throughout the drawings, wherein.

DETAILED DESCRIPTION

The following description presents exemplary systems and methods for enhanced tomographic imaging using emission and anatomical scan data. Particularly, embodiments illustrated hereinafter disclose a hybrid PET/MRI system and method that allow for simultaneous PET attenuation correction and PET image reconstruction via selective update of conventionally ambiguous image-regions using acquired PET and MRI information.

Although exemplary embodiments of the present systems and methods are described in the context of correction of PET and/or PET/MR images, the embodiments described herein are also applicable to attenuation correction and/or image modification in other modalities. For example, the disclosed embodiments may be used in other imaging systems such as PET/CT, single photon emission computed tomography (SPECT)/MRI, SPECT/CT, PET/electrical impedance tomography (EIT), SPECT/optical imaging systems, and/or SPECT/EIT systems. Further, in addition to medical imaging, embodiments of the systems and methods discussed herein may also be used in pharmacological and pre-clinical research for the development and evaluation of innovative tracer compounds.

Additionally, it may be noted that the embodiments of image data acquisition described herein may be performed sequentially, such as by first obtaining PET image data followed by the acquisition of MRI data, or vice versa. Alternatively, the image data acquisition may be performed substantially simultaneously via simultaneous acquisition of PET and MRI data for use in simultaneous attenuation correction and image reconstruction. An exemplary environment that is suitable for practicing various implementations of the present disclosure is discussed in the following sections with reference to FIG. 1.

Figure 1:
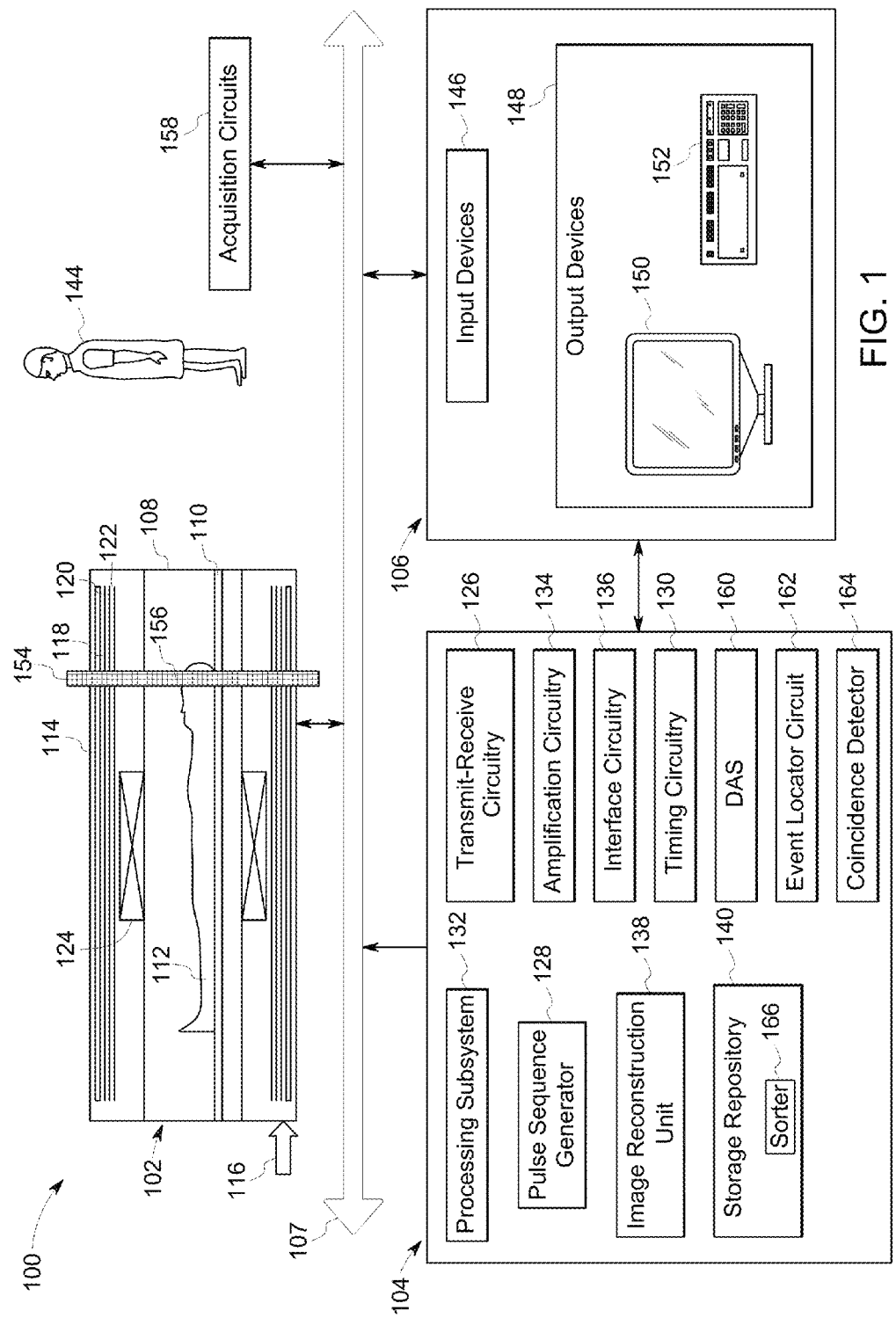
FIG. 1 is a schematic view of an embodiment of a hybrid imaging system configured to obtain attenuation-corrected emission images, in accordance with an aspect of the present specification.

FIG. 1 illustrates an exemplary imaging system 100 for enhanced emission tomography imaging. Particularly, in one embodiment, the system 100 corresponds to a PET/MRI system configured to provide enhanced PET attenuation correction and PET image reconstruction using MRI data. Although, FIG. 1 illustrates a hybrid PET/MRI system, in certain embodiments, the system 100 may include independent PET and MRI systems for imaging a subject. Alternatively, the system 100 may include other imaging systems such as a PET/CT, PET/EIT, PET/optical imaging, SPECT/MRI, SPECT/CT, SPECT/EIT, and/or a SPECT/optical imaging system configured for enhanced emission tomography imaging of the subject using corresponding anatomical scan data.

Particularly, in one embodiment, the system 100 includes a scanner 102, a system controller 104, and an operator interface 106 that are communicatively coupled to each other over a communications network 107 for imaging the subject. The communications network 107, for example, may include wired and/or wireless communication links corresponding to a backplane bus, a short-range network, a local area network, a wide area network, and/or the Internet. In certain embodiments, the scanner 102 performs simultaneous MR and PET imaging scans of the subject based on one or more control signals received from the system controller 104 via the communications network 107.

To that end, in one embodiment, the scanner 102 includes a bore 108 into which a table 110 may be positioned for disposing the subject such as a patient 112 in a desired scanning position. Moreover, the scanner 102 may also include a series of associated coils for imaging a target volume in the patient 112. Particularly, in one embodiment, the scanner 102 includes a primary magnet coil 114, for example, energized via a power supply 116 for generating a primary magnetic field generally aligned with the patient bore 108. The scanner 102 may further include a series of gradient coils 118, 120 and 122 grouped in a coil assembly for generating accurately controlled magnetic fields, the strength of which vary over a designated field of view (FOV) of the scanner 102.

Additionally, in certain embodiments, the scanner 102 may also include a radiofrequency (RF) coil 124 configured to generate RF pulses for exciting a gyromagnetic material that is typically bound in tissues of the patient 112. In one embodiment, the RF coil 124 may also serve as a receiving coil. Accordingly, the RF coil 124 may be operationally coupled to transmit-receive circuitry 126 in passive and/or active modes for receiving emissions from the gyromagnetic material and for applying RF excitation pulses, respectively.

In certain embodiments, the system controller 104 may be configured to control operation of the MR coils 118, 120, 122, and 124 for generating the desired magnetic fields and/or for applying the RF excitation pulses. Accordingly, in one embodiment, the system controller 104 may include a pulse sequence generator 128, timing circuitry 130, and a processing subsystem 132 for generating and controlling imaging gradient waveforms and RF pulse sequences employed during patient examination. Particularly, in one embodiment, the pulse sequence generator 128 may be configured to generate a T1-weighted, T2-weighted, T2*-weighted, susceptibility-weighted, proton density-weighted, fat selective, water selective, and/or Dixon pulse sequences for acquiring desired MRI data.

Further, in certain embodiments, the system controller 104 may include amplification circuitry 134 and interface circuitry 136 configured to control and/or interface between the pulse sequence generator 128 and the coils of the scanner 102. For example, the amplification circuitry 134 and/or the interface circuitry 136 may be configured to drive the RF coil 124 and amplify corresponding MRI response signals for further processing. Additionally, in certain embodiments, the amplification and/or interface circuitry 134-136 may also be configured to amplify response signals, such as electrocardiogram (ECG) signals, received from one or more sensors (not shown) operatively coupled to the patient 112.

The amplified response signals, in turn, may be transmitted to the processing subsystem 132 for determining information for use in image reconstruction. Particularly, in one embodiment, the processing subsystem 132 demodulates, filters, and/or digitizes the received response signals for generating the processed image reconstruction information. Further, the processing subsystem 132 may apply selected analytical routines to the processed information for deriving clinically useful indicators such as location of a stenosis and structural and/or functional parameters such as blood flow in the target volume. Accordingly, in one embodiment, the processing subsystem 132 may include devices such as one or more application-specific processors, graphical processing units (GPUs), digital signal processors (DSPs), microcomputers, microcontrollers, Application Specific Integrated Circuits (ASICs) and/or Field Programmable Gate Arrays (FPGAs).

Further, in certain embodiments, the processing subsystem 132 stores the processed information and/or the clinically useful indicators in a storage repository 140. In one embodiment, the storage repository 140 may also store physical and logical axis configuration parameters, pulse sequence descriptions, and/or programming routines for use by the scanner 102. Additionally, in certain embodiments, the storage repository 140 may further store programming code for implementing one or more algorithms capable of performing PET attenuation correction and/or PET image reconstruction based on acquired MRI data in accordance with an aspect of the present specification. To that end, the storage repository 140 may include devices such as a hard disk drive, a floppy disk drive, a compact disk-read/write (CD-R/W) drive, a Digital Versatile Disc (DVD) drive, a flash drive and/or a solid-state storage device.

Additionally or alternatively, in certain other embodiments, the processing subsystem 132 transmits the processed information and/or the clinically useful indicators to an image reconstruction unit 138 to allow reconstruction of desired images of the target volume. Particularly, the image reconstruction unit 138 may be configured to reconstruct an MR image corresponding to the target volume in the patient 112. The target volume, for example, may correspond to one or more biological tissues such as hepatic, neural, or cardiac tissues in the patient 112. Alternatively, in embodiments, where the system 100 is used for non-medical imaging, the target volume may correspond to a selected region of interest in a non-biological object.

In one embodiment, the target volume may be selected by an operator 144 via the operator interface 106. Additionally, the operator interface 106 may allow the operator 144 to specify commands and scanning parameters via one or more input devices 146 for use during the MRI and/or PET scan. To that end, the operator interface 106 may provide one or more selectable and/or definable options on one or more of the input devices 146 for configuring imaging parameters such as table motion, patient orientation, table orientation, and/or imaging pulse sequences. Further, in certain embodiments, the operator interface 106 may also include options for requesting a desired output of MR images, PET images, and/or corresponding diagnostic information.

Particularly, in certain embodiments, the operator interface 106 includes one or more output devices 148 such as a display 150 and/or a printer 152 for receiving the requested output information. The display 150, for example, may be integrated into wearable eyeglasses, or may be ceiling or cart mounted to allow the interventional practitioner 144 to observe the reconstructed images, data derived from the images and other relevant information such as scanning time throughout the procedure. In one embodiment, the display 150 may include an interactive user interface that may also allow selection and display of scanning modes, FOV, and prior exam data. Additionally, the interactive user interface may allow on-the-fly access to patient data such as respiration and heart rate, scanning parameters, and/or options for selection of an ROI for subsequent imaging.

Thus, during a medical examination, MRI allows determination of structural and/or functional information of the target volume that may aid in diagnosis, prescribing treatment, and/or as complementary information for studying complex biochemical processes. In certain embodiments, the structural information derived from MRI images may be used for determining attenuation coefficients for use in PET image reconstruction. To that end, the PET data may be acquired sequentially and/or substantially simultaneously with the MR data acquisition.

Particularly, in one embodiment, a positron emitter or a radiotracer may be administered to the patient 112 that targets specific tissues corresponding to the target volume in the patient's body. Further, in certain embodiments, the system 100 includes a detector ring assembly 154 that is disposed about the patient bore 108 and is configured to detect radiation events corresponding to the target volume. In one embodiment, the detector ring assembly 154 includes multiple detector rings that are spaced along the central axis of the system 100. The detector rings contain a plurality of detector modules 156, which in turn, may include a 6×6 array of individual bismuth germanate (BGO) detector crystals. Generally, the detector modules 156 may be used to detect gamma radiation emitted from the patient 112 and may produce photons in response to the detected gamma radiation.

Accordingly, in one embodiment, the array of detector modules 156 are positioned proximate to a plurality of photomultiplier tubes (not shown) in the system 100. In certain embodiments, the photomultiplier tubes (PMTs) are configured to produce analog signals when a scintillation event occurs at one of the detector modules 156. Specifically, the PMTs may be configured to produce analog signals when a gamma ray emitted from the patient is received by one of the detector modules 156. Further, the system 100 may also include a set of acquisition circuits 158 that may be configured to receive the analog signals and generate corresponding digital signals. In one embodiment, the digital signals are indicative of a location and energy associated with a detected radiation event, and thus, may be used during PET image reconstruction.

In certain embodiments, the system 100 further include a data acquisition system (DAS) 160 that may be configured to periodically sample the digital signals produced by the acquisition circuits 158. The DAS 160, in turn, may include one or more event locator circuits 162 configured to assemble information corresponding to each valid radiation event into an event data packet. The event data packet, for example, may include a set of digital numbers that may accurately indicate a time of the radiation event and a position of the detector crystal that detected the radiation event.

Further, in one embodiment, the event locator circuits 162 communicate the assembled event data packets to a coincidence detector 164 for determining coincidence events. Particularly, the coincidence detector 164 determines coincidence event pairs if time and location markers in two event data packets are within certain designated thresholds. By way of example, in one embodiment, the coincidence detector 164 may be configured to identify a coincidence event pair if time markers in two event data packets are within 12 nanoseconds of each other and if the corresponding locations lie on a straight line passing through a field of view (FOV) across the patient bore 108.

In certain embodiments, the system 100 stores the determined coincidence event pairs in the storage repository 140. The storage repository 140, in one embodiment, includes a sorter 166 to sort the coincidence events, for example, in a 3D projection plane format using a look-up table. Particularly, the sorter 166 orders the detected coincidence event data using one or more parameters such as radius or projection angles for efficient storage. In one embodiment, the processing subsystem 132 processes the stored data to determine time-of-flight (TOF) and/or non-TOF information. The TOF information may allow the PET/MRI system 100 to estimate a point of origin of the electron-positron annihilation with greater accuracy, thus improving event localization.

In certain embodiment, the event localization information may be used to further enhance the quality of PET images reconstructed by the image reconstruction unit 138. Particularly, the event localization information may be used to reconstruct a PET activity or emission map (or image) that defines a spatial distribution of a radiotracer in the patient body based on the emitted 511 keV photons measured by the detector modules 156. Typically, the emitted photons travel through different regions of the patient body or extra-patient components such as tissue, lungs, air, beds and/or MR coils, and thus, experience different attenuations.

Certain conventional imaging approaches entail correcting the attenuation values in the activity maps using MRI information determined via segmentation and/or atlas-based registration of the MR images. However, as previously noted, such conventional approaches may result in inaccurate attenuation correction in and/or near ambiguous image-regions such as bones, metal implants, air, and lungs due to insufficient visualization of these regions in the MR images.

Unlike such conventional approaches, the image reconstruction unit 138 jointly estimates attenuation in the sinogram space and an emission activity map from PET and MRI data. Particularly, in one embodiment, attenuation factors corresponding to lines of response (LORs) passing through distinctive image-regions such as fat and water that can be reliably determined from MR scan data are calculated by forward-projecting known attenuation coefficient values along the LORs. Further, attenuation factors that correspond to lines of response (LORs) passing through the ambiguous image-regions that are indistinguishable in the MR images may be selectively updated using PET emission scan data.

Thus, the image reconstruction unit 138 allows for simultaneous estimation of both the complete emission activity map and any undetermined attenuation factors in projection-space corresponding to the ambiguous image-regions using the determined attenuation factors. The accurately determined PET activity map and the projection-space attenuation factors, in turn, allow reconstruction of high quality TOF and/or non-TOF PET images and/or provide the operator 144 with corresponding diagnostic information. Particularly, in one embodiment, the PET images and the corresponding diagnostic information may be communicated to the operator 144 via one or more of the output devices 148, such as the display 150, the printer 152, and/or an audio-video device coupled to the operator interface 106. Communicating the enhanced attenuation-corrected PET images and/or diagnostic information allows a medical practitioner to assess a health condition of the patient 112 with greater accuracy.

It may be noted that the specific arrangements depicted in FIG. 1 are exemplary. Further, the system 100 may be configured or customized for additional functionality, different imaging applications and scanning protocols. Accordingly, in certain embodiments, the system may be coupled to multiple displays, printers, workstations, and/or similar devices located either locally or remotely, for example, within an institution or hospital, or in an entirely different location via the one or more configurable wired and/or wireless networks 107 such as the Internet, cloud computing, and/or virtual private networks.

By way of example, in one embodiment, the system 100 may be coupled to a picture archiving and communications system (PACS) to store the resulting MR and attenuation-corrected PET images. Additionally, the system 100 may be coupled to other remote systems such as a radiology department information system, a hospital information system, and/or to an internal or external network to allow operators at different locations to supply commands and parameters and/or gain access to the PET attenuation factors and/or enhanced PET images. An exemplary method for enhanced emission tomographic imaging using joint estimation will be described in greater detail with reference to FIG. 2.

Figure 2:
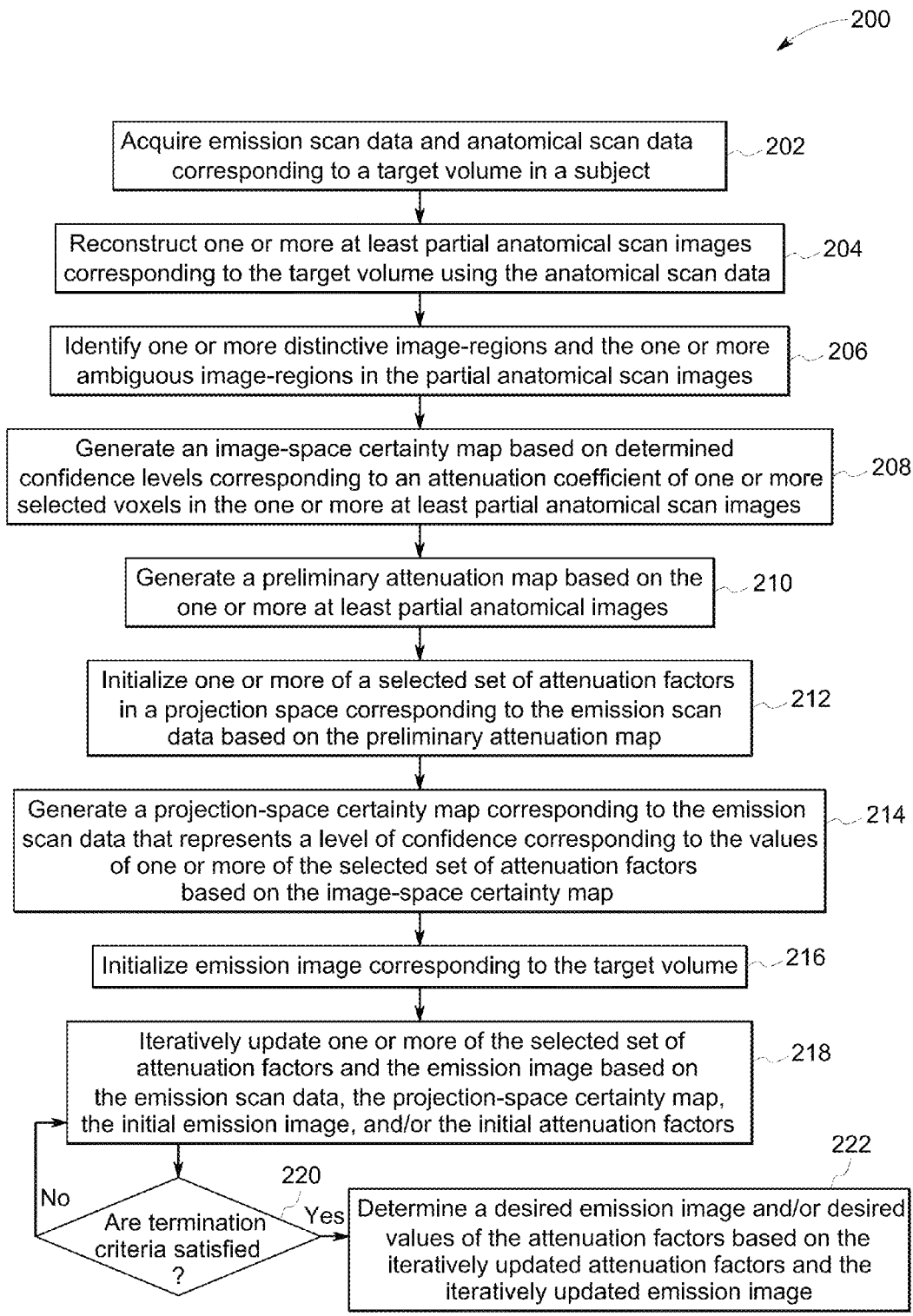
FIG. 2 is a flowchart depicting an exemplary method for enhanced tomographic imaging of a target volume in a subject, in accordance with aspects of the present specification.

FIG. 2 illustrates a flow chart 200 depicting an exemplary method for enhanced emission tomography imaging. In the present specification, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract image data types.

Additionally, embodiments of the exemplary method may also be practised in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 2, the exemplary method is illustrated as a collection of blocks in a logical flow chart, which represents operations that may be implemented in hardware, software, or combinations thereof. The various operations are depicted in the blocks to illustrate the functions that may be performed, for example, during the steps of generating the image-space certainty map and/or determining a desired emission image and desired values of the attenuation factors in the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIG. 1.

Emission tomography imaging allows for generation of two-dimensional (2D) and/or three-dimensional (3D) images that provide structural and/or functional information corresponding to a target volume. Accordingly, the emission images find use in study of complex biochemical processes and/or detecting disease conditions based on certain image-derived parameters. Particularly, the image-derived parameters may be used in diagnosing and/or prescribing a suitable treatment for a patient. Accuracy of the diagnosis and/or treatment prescription, thus, depends upon accurate reconstruction of an emission activity map, which in turn, depends upon accurate attenuation correction of the emission scan data.

Accordingly, the following description discloses an embodiment of the present method that allows for simultaneous estimation of activity and attenuation using emission scan data acquired from an emission tomography system and anatomical scan data such as MRI scan data received from an anatomical scan system. Particularly, the present method entails use of anatomical scan data in addition to the emission scan data to determine accurate attenuation values even for regions in the target volume that are conventionally difficult to classify using the anatomical scan data.

The method begins at step 202, where emission scan data and anatomical scan data corresponding to a target volume in a subject is acquired. The emission scan data, for example, may be acquired using an emission tomography system such as the PET/MRI system 100 of FIG. 1. Further, the anatomical scan data may be acquired, for example, using anatomical scan systems such as an MRI system, a CT imaging system, an X-ray imaging system, an EIT system, and/or an optical imaging system. Moreover, in certain embodiments, the emission and anatomical scan data are acquired using a respiratory and/or cardiac gating pulse sequence.

Particularly, in one embodiment, a radiotracer such as Fluorodeoxyglucose (FDG) may be administered to the patient for acquiring the emission scan data corresponding to a target volume. The target volume may correspond to biological tissues, for example, liver or lung tissues corresponding to the patient. In certain embodiments, the PET/MRI system 100 acquires the PET emission scan data corresponding to the target volume during an estimated decay period of the radiotracer. Specifically, measured values representative of an uptake distribution of the radiotracer in the target volume as a function of time may be used for reconstructing desired 2D and/or 3D images of the target volume. Further, the reconstructed images may aid in an assessment of one or more functional and/or physiological parameters, such as blood flow, in the target volume.

To that end, in one embodiment, the acquired PET data may be stored along with time-of-flight (TOF) information corresponding to a measured difference in time between arrivals of each pair of gamma photons from each annihilation event for use in PET image reconstruction. In another embodiment, the PET/MRI system 100 stores the acquired PET data without TOF information. Particularly, in certain embodiments, the acquired PET data may be stored in a list-mode and/or a sinogram format.

Further, in certain embodiments, the anatomical scan data may be acquired by an anatomical scan system, such as the PET/MRI system 100, before, after, and/or during the PET data acquisition. In one embodiment, the system 100 uses Liver Acquisition with Volume Acquisition (LAVA), LAVA flex, localizer, ultrashort echo time (UTE), zero echo time (ZTE), and/or gapped three-dimensional (3D) grid MR sequences for acquiring the MRI data. Additionally, in certain embodiments, the system 100 optimizes the MRI contrast used during the MRI data acquisition. The MRI contrast, for example, may be T1-weighted (T1w), proton density weighted (PDw), T2 weighted (T2w), and/or for segmenting a particular tissue type and/or to avoid certain artifacts. Moreover, in some embodiments, the system 100 may also pre-process the MRI data, for example, to aid in a three-dimensional gradient linearity correction in resulting MR images.

Moreover, at step 204, one or more at least partial anatomical scan images are reconstructed using the anatomical scan data. Specifically, in one embodiment, the MRI scan data may be used for reconstructing in-phase ($I_i$), out-of-phase ($I_o$), water ($I_w$), fat ($I_f$), proton density-weighted, UTE, ZTE, localizer, and/or gapped 3D grid images. In certain embodiments, the MR data acquisition performed within a same repetition time (TR) may obtain all four images corresponding to in-phase, out-of-phase, water, and fat for a particular slice selection, and may be extended for generating MR images of the whole body of the patient. By way of example, the system 100 may be configured to reconstruct the desired MR images corresponding to the target volume using Dixon and/or Iterative Decomposition of water and fat with Echo Asymmetry and Least squares estimation (IDEAL) methods.

Further, at step 206, one or more distinctive and one or more ambiguous image-regions are identified in the one or more at least partial anatomical scan images. Typically, the anatomical scan images such as the MR images provide anatomical information with high spatial resolution and soft tissue contrast. Accordingly, MR images provide efficient visualization or classification of water, fat, and/or soft tissues. Thus, these regions correspond to distinctive image-regions. Particularly, as used herein, the term "distinctive image-regions" is used to refer to the image-regions that have classifiable tissue types and for which a PET attenuation coefficient may be reliably determined.

However, MRI provides poor visualization of proton deficient regions such as bone, metal, air, and/or lungs even though these materials exhibit different PET attenuation values. Thus, the MR image may include one or more ambiguous image-regions corresponding to a location of such proton deficient materials in the target volume. Moreover, in one embodiment, truncation of a field of view of the MRI system may also result in low or no MRI signals in the truncated regions, which may be represented as ambiguous image-regions in the MR image. Accordingly, as used herein, the term "ambiguous image-regions" is used to refer to image-regions having uncertain classification and for which a PET attenuation coefficient may not be reliably determined.

According to certain aspects of the present specification, in certain embodiments, the MR images may undergo bias field correction before identifying the one or more distinctive and/or ambiguous image-regions. Additionally, segmentation, atlas-based registration, machine learning, and/or MRI pulse sequences such as LAVA flex, IDEAL MRI, ultra-short echo time (UTE), and/or zero echo time (ZTE) may be used to identify one or more distinctive and/or ambiguous image-regions in the MR images. For example, use of the LAVA flex sequence or the IDEAL MRI pulse sequence may allow for identification of distinctive water and fat image-regions in the MR images with a desired confidence level. Alternatively, the MR images may be segmented, for example, based on thresholding, partial differential equations (PDE), atlas-based or template-based registration, a multi-scale model, machine learning, region growing, and/or active contour methods to identify the distinctive and/or ambiguous image-regions.

Particularly, in certain embodiments, the MR images may be segmented based on threshold values which, for example, are determined using a first local minimum of a histogram generated using voxel values corresponding to one or more of the MR images and/or one or more regions of interest in the MR images. Further, in one embodiment, regions whose voxel values are smaller than the threshold values may be determined as ambiguous image-regions in the MR images. In another embodiment, prior anatomical knowledge may be used in identifying the one or more ambiguous image-regions. For example, regions that are likely to contain vertebrae may be identified as ambiguous image-regions based on a location of lungs in the target volume that may be determined using segmentation. However, in the present method, the ambiguous image-regions need not necessarily correspond to an organ or a classifiable segment boundary, but rather may correspond to voxels that cannot be accurately identified with a desired confidence level. Thus, in certain embodiments, boundary regions between identified segments may be labeled as ambiguous image-regions due to an uncertainty caused by partial volume effects.

Further, in some embodiments, the distinctive and/or ambiguous image-region in an MR image may be identified based on a data acquisition protocol or the field of view (FOV) of the scanner. By way of example, regions truncated due to a small FOV of the system 100, and/or regions reconstructed with insufficient image quality may be identified as the ambiguous image-regions. Moreover, in one embodiment, regions in the MR images, where the MRI data is unavailable or undetermined due to use of an MRI localizer scan or MRI scan on 3D gapped grids may also be identified as ambiguous image-regions.

Further, at step 208, an image-space certainty map is generated. The image-space certainty map represents a degree of confidence in the attenuation coefficient or attenuation value assigned to one or more selected voxels in one or more at least partial anatomical scan images. In certain embodiments, the image-space certainty map may be binary. Accordingly, in one embodiment, if there is sufficient confidence in the attenuation value assigned to a voxel, the corresponding voxel of the image-space certainty map is set to one, or else the voxel in the image-space certainty map is set to zero.

For example, voxels corresponding to the distinctive image-regions in the MR image may be assigned a value of one, whereas the voxels corresponding to the ambiguous image-regions may be set to zero. In certain embodiments, if a voxel belongs to both the distinctive image-regions and the ambiguous image-regions, then the corresponding voxel of the image-space certainty map may be set to zero. In certain other embodiments, voxels in the image-space certainty map may be assigned continuous values from a selected range such that voxels corresponding to distinctive image-regions are assigned, for example, higher values in the image-space certainty map, whereas other pixels are assigned lower values.

Additionally, at step 210, a preliminary attenuation map is generated based on the one or more at least partial anatomical images. In certain embodiments, known attenuation values are assigned to the one or more distinctive image-regions and selected attenuation values are assigned to the one or more ambiguous image-regions identified at step 206. In one embodiment, the known attenuation values corresponding to the distinctive image-regions such as fat, water, and soft tissues may be determined from clinically prescribed lookup tables. The lookup tables may store one or more correlations between different tissues types and/or constituent materials in the distinctive image-regions and their corresponding attenuation values, thus allowing for appropriate assignment of attenuation values to each of the distinctive image-regions in the MR image.

Further, in certain embodiments, selected attenuation values may be assigned to the ambiguous image-regions in the at least partial MR images. Generally, the attenuation map represents a distribution of linear attenuation coefficients or attenuation values corresponding to emission photons. Accordingly, in one embodiment, the attenuation map is generated based on the known and selected attenuation values assigned to each pixel and/or voxel in distinctive and/or ambiguous image-region identified in the at least partial MR images. In certain embodiments, the attenuation values corresponding to the preliminary attenuation map may be selected randomly from attenuation values corresponding to a selected list of ambiguous materials in the stored lookup table. Alternatively, the attenuation values may be selected based on anatomical context and/or predetermined patient information such as presence of implants. Accordingly, in certain embodiments, the preliminary attenuation map may be correlated with the at least partial MR images, for example, based on image segmentation, an anatomical atlas-based image registration, a predetermined template-based image registration, and/or via machine learning that employs MR images, and/or a bilinear transformation using X-ray CT images.

Moreover, at step 212, one or more of a selected set of attenuation factors in a projection space corresponding to the emission scan data are initialized based on the preliminary attenuation map. The selected set of attenuation factors may correspond to all of the attenuation factors, or one or more subsets of the attenuation factors selected for use in different imaging stages and/or imaging goals. In one embodiment, a relationship between the preliminary image-space attenuation map and attenuation factors in the sinogram space is determined using the Beer-Lambert law. Specifically, given the preliminary attenuation map generated at step 210, initial attenuation factors may be determined by calculating the forward-projection of the preliminary attenuation map followed by computing an exponential function of negative forward-projection values.

Additionally, at step 214, a projection-space certainty map that represents a level of confidence corresponding to the value of one or more of the selected set of attenuation factors is determined based on the image-space certainty map generated at step 208. Particularly, in one embodiment, a binary projection-space certainty map may be calculated from the binary image-space certainty map. To that end, the binary image-space certainty map is negated such that values of voxels are changed from one to zero and vice versa. The negated image-space certainty map is then forward-projected. Further, the binary projection-space certainty map is constructed such that a bin in the projection-space certainty map is set to zero if a corresponding forward-projection value is non-zero. Alternatively, the bin in the projection-space certainty map is set to one if a corresponding forward-projection value is zero. Thus, if a LOR passes through a voxel corresponding to an ambiguous image-region whose image-space certainty value is zero, then the corresponding projection-space certainty value is set to zero. Such LORs, thus, also correspond to ambiguous projection-regions. Alternatively, if a LOR passes only through voxels corresponding to a distinctive image-region whose image-space certainty value is one, then the corresponding projection-space certainty value is set to one to generate the binary projection-space certainty map. Such LORs, thus, also correspond to distinctive projection-regions.

Further, in certain other embodiments, a continuous-valued projection-space certainty map may be determined by calculating a forward-projection of the binary or continuous-valued image-space certainty map. Alternatively, the continuous-valued projection-space certainty map may be determined by normalizing the forward-projection values, which are weighted sums of the image-space certainty map values generated at step 208.

Moreover, at step 216, an emission image corresponding to the target volume is initialized. In one embodiment, the emission image may be initialized based on a uniform image. Alternatively, the emission image may be initialized based on an image reconstructed by filtered backprojection (FBP) or ordered subset expectation maximization (OSEM) using the preliminary attenuation map generated at step 210.

Further, at step 218, the emission image and one or more of the selected set of attenuation factors corresponding to at least the one or more ambiguous projection-regions are iteratively updated based on the emission scan data, the projection-space certainty map, the initial emission image, and the one or more initial attenuation factors. In one embodiment, the initial emission image and the projection-space attenuation map may be updated alternately until one or more selected termination criteria are satisfied. For example, in one iteration, the initial emission image may be updated based on the initial attenuation factors. Further, in a subsequent iteration, the initial attenuation factors may be updated based on the updated emission image.

Particularly, as previously noted, the emission image may be initialized using a uniform image and/or a predetermined emission image. Subsequently, the initialized emission image may be updated, for example, using a maximum likelihood (ML), penalized likelihood (PL), or Bayesian maximum a posteriori (MAP) framework. Particularly, in certain embodiments, the emission image may be iteratively updated, for example, using an ordered subset expectation maximization (OSEM), expectation maximization (EM), block sequential regularized expectation maximization (BSREM), and/or preconditioned conjugate gradient (PCG)-based method.

Additionally, regularization of the iterative update may be performed using one or more penalty functions. In one example, penalty functions such as quadratic penalties, Huber penalties, generalized Gaussian penalties, and/or relative difference penalties may be used to penalize differences between values of neighboring voxels. Alternatively, penalty functions that include prior distributions of attenuation coefficients such as multi-modal or Gaussian mixture distributions may be used to penalize deviations from a selected or a reference attenuation map. In certain embodiments, the iterative update may also entail use of sums of voxel values that are available in certain regions of the emission image as constraints during the update of the emission image.

Similarly, the attenuation factors corresponding to the ambiguous projection-regions may be initialized using the initial attenuation factors determined at step 212 and/or using predetermined attenuation factors. Further, the attenuation factors may be updated, for example, using OSEM, EM, ordered subset separable paraboloidal surrogate (OS-SPS), and/or PCG-based methods.

Additionally, the iterative update of the attenuation factors may also employ regularization or penalty functions that penalize differences between neighboring bins in certain determined directions. These directions, for example, include transaxial radial, transaxial (azimuthal) angular, axial and polar angular directions. In certain embodiments, the iterative update entails calculating upper bounds for one or more selected attenuation factors based on the preliminary attenuation map, the image-space certainty map, and the projection-space certainty map. Further, one or more inequality constraints based on the initial attenuation factors may be applied during update of the attenuation factors.

Alternatively, a parametric model and one or more parameters that parameterize the parametric model are determined to represent the selected attenuation factors. By way of example, the parametric model includes an inverse Fourier rebinning or inverse single slice rebinning. Further, the parameters include one or more attenuation factors corresponding to direct plane LORs. Accordingly, in one embodiment, the parameters corresponding to the initialized attenuation factors are initialized. Moreover, during the iterative update, the attenuation factors corresponding to oblique planes are parameterized by the attenuation factors corresponding to direct planes through inverse Fourier rebinning or inverse single-slice rebinning. However, only the direct-plane attenuation factors may be updated. As a number of direct-plane attenuation factors is generally known to be much smaller than that of oblique-plane attenuation factors, a number of unknowns to estimate during the iterative updates is substantially reduced. It may be noted that, in certain embodiments, the initial attenuation factors and an initial emission image may be iteratively updated, for example, until the selected termination criteria are satisfied.

Accordingly, at step 220, it may be determined if one or more termination criteria are satisfied for terminating the iterative update of the emission image and the attenuation factors. The termination criteria, for example, includes a verification step to check if a desired number of iterations is performed and/or if a determined difference between the current and the previous iterate is smaller than a predetermined value.

If the termination criteria are not satisfied at step 220, control passes back to step 218 and the iterative update of the emission image and the attenuation factors continue. However, if at step 220, the termination criteria are satisfied, control passes to step 222.

Particularly, at step 222, a desired emission image and/or desired values of the one or more attenuation factors are determined based on the iteratively updated emission image and the iteratively updated attenuation factors. In one embodiment, the emission image and the attenuation factors determined during the final iteration at step 220 are used as the desired emission image and the desired attenuation factors. Alternatively, the desired PET emission image may be re-reconstructed from the PET emission scan data using the attenuation factors determined during the final iteration of step 220 and emission tomography image reconstruction algorithms. The emission tomography image reconstruction algorithms, for example, include OSEM, BSREM, PCG, SPS and its ordered subsets (OS) version and/or De Pierro's modified expectation maximization and its OS version.

An exemplary mathematical description of the present method described with reference to FIG. 2 is described herein.

In one embodiment, TOF PET emission sinogram data $y_{ik}$, acquired at step 202, may be modeled as independent Poisson random variables that may be represented using equation (1).

$$E[y_{ik}] = \bar{y}_{ik}(\lambda, \alpha) \equiv \alpha_i s_{ik}(\lambda) + r_{ik} \quad (1)$$

for $i=1, \ldots, N_b$ and $k=1, N_t$
where i and k corresponds to LOR index and TOF bin index, respectively, $N_b$, $N_t$, and $N_v$ correspond to number of sinogram bins, TOF bins, and image voxels, respectively, $\lambda$ corresponds to an $N_v$ by 1 column vector representing the emission image, $\alpha$ corresponds to an $N_b$ by 1 column vector whose elements $\alpha_i$ represent attenuation factors, $s_{ik}$ corresponds to an unattenuated TOF forward projection of the emission image, and $r_{ik}$ corresponds to mean contribution of randoms and scatters.

In one embodiment, the unattenuated TOF forward projection may be represented using equation (2).

$$s_{ik}(\lambda) = \sum_j a_{ij}^k \lambda_j \quad (2)$$

where $a_{ij}^k$ corresponds to a TOF forward projector including normalization and detector blurring.

In a presently contemplated embodiment, the emission image $\lambda$ and the attenuation factors $\alpha_i$ may be estimated given the TOF PET sinogram data $y_{ik}$, and values corresponding to the background contributions $r_{ik}$ that may be estimated using predetermined information. Particularly, the attenuation factors may be represented using equation (3).

$$\alpha_i = \exp(-\sum_j g_{ij} \mu_j) \quad (3)$$

where $g_{ij}$ corresponds to a non-TOF geometric forward projector, which models the length of LOR i that intersects with voxel j, and $\mu$ corresponds to an $N_v$ by 1 column vector representing the attenuation map, whose elements $\mu_j$ correspond to a linear attenuation coefficient of voxel j for 511 keV photons.

Further, the non-TOF geometric forward projector may be implemented using Siddon's method or distance-driven projectors. In an embodiment where attenuation coefficients are known for a certain set J of voxels in the attenuation map, for example, represented using equation (4), $$\mu_j = \mu_j^{known} \text{ for } j \in J \quad (4)$$

the attenuation factors may be rewritten using equations (5), (6) and (7).

$$\alpha_i = \gamma_i \exp(-\sum_{j \in J'} g_{ij} \mu_j) \quad (5)$$

$$\text{where } \gamma_i \equiv \exp(-\sum_{j \in J} g_{ij} \mu_j^{known}) \text{ and} \quad (6)$$

$$J' \equiv \{j=1, \ldots, N_v: j \text{ does not belong to } J\} \quad (7)$$

where J corresponds to the distinctive image-regions, J' corresponds to the ambiguous image-regions as identified at step 206, and $\mu_j^{known}$ may be determined in step 210. It holds that $\alpha_i \leq \gamma_i$ since $g_{ij} \geq 0$ and $\mu_j \geq 0$.

Accordingly, in one embodiment, a binary image-space certainty map may be determined using equation (8), as generated at step 208.

$$\zeta_j = 1 \text{ if } j \in J \text{ and } \zeta_j = 0 \text{ if } j \in J' \quad (8)$$

In an embodiment, where the LOR i passes only through voxels with known attenuation coefficients in J, the corresponding attenuation factor $\alpha_i$ has a known value $\gamma_i$. Thus, the LOR i belongs to the distinctive projection-regions. Accordingly, the set of such LORs may be represented, for example, using equation (9).

$$\bar{I} \equiv \{i: \text{For all } j, \text{ if } g_{ij} \neq 0, \text{ then } j \in J\} \quad (9)$$

where $\bar{I}$ represents the distinctive projection-regions.

Further, the attenuation factors may be represented using equation (10).

$$\alpha_i = \gamma_i \text{ if } i \in \bar{I} \quad (10)$$

where $\gamma_i$ is calculated using equation (6) for $i \in \bar{I}$ and may be determined as described in step 212.

Alternatively, when $i \in I \equiv \{i: \text{there exists } j \text{ such that } g_{ij} \neq 0 \text{ and } j \text{ does not belong to } J\}$, $\alpha_i$ is unknown and may be estimated. Here, I represents the ambiguous projection-regions. Thus, a binary projection-space certainty map $\xi$, such as the map generated at step 214, may be determined using equation (11).

$$\xi_i = 1 \text{ if } i \in \bar{I} \text{ and } \xi_i = 0 \text{ if } i \in I \quad (11)$$

Further, a penalized-likelihood (PL) objective function for use in the iterative update may be represented using equation (12).

$$\Phi(\lambda, \alpha) = \sum_{i,k} y_{ik} \log \bar{y}_{ik}(\lambda, \alpha) - \bar{y}_{ik}(\lambda, \alpha) - R_\lambda(\lambda) - R_\alpha(\alpha) \quad (12)$$

where $R_\lambda(\lambda)$ corresponds to the regularization or penalty function for the emission image and $R_\lambda(\alpha)$ corresponds to the regularization or penalty function for the attenuation factors. It may be noted that when the penalty functions are all zero, the objective function corresponds to the (log) likelihood function.

Maximizing the PL objective function with respect to the activity image $\lambda$ and the attenuation factors $\alpha$ subject to constraints that $\lambda_j \geq 0$ for all j, $\alpha_i \leq \gamma_i$ for $i \in I$, and $\alpha_i = \gamma_i$ for $i \in \bar{I}$ leads to estimated emission image and attenuation factors. As previously noted with reference to step 218, the emission image $\lambda$ and attenuation factors $\alpha$ may be alternatively updated, for example, using OSEM or OSSPS and modified EM, respectively.

The resulting emission images and/or the attenuation factors allow for accurate quantitation of tracer uptake, for example, for detecting and staging cancers and monitoring response to treatment. FIGS. 3-17 depict certain simulated images that are indicative of a performance of an exemplary implementation of the method described with reference to FIG. 2.

Figure 3:
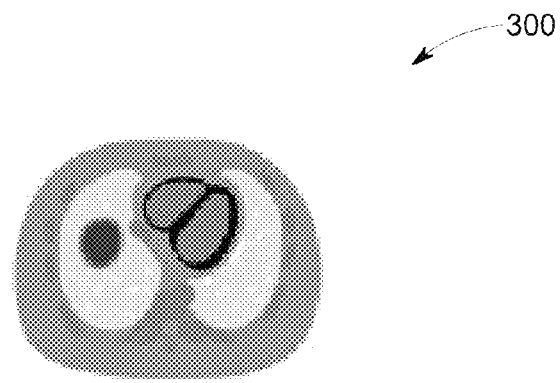
FIGS. 3 and 4 illustrate transaxial and coronal slices of an embodiment of a true emission image, respectively.
Figure 4:
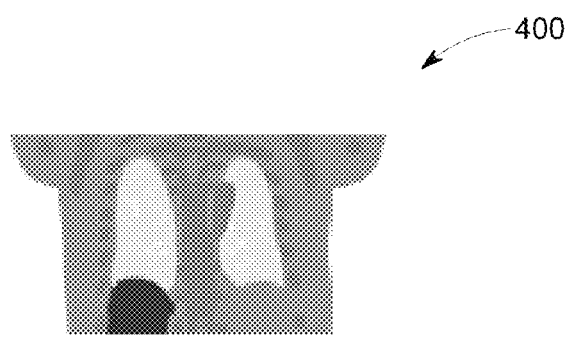
Figure 5:
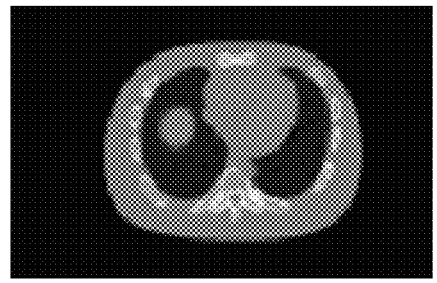
FIGS. 5 and 6 illustrate transaxial and coronal slices corresponding to an embodiment of a true attenuation map, respectively.
Figure 6:
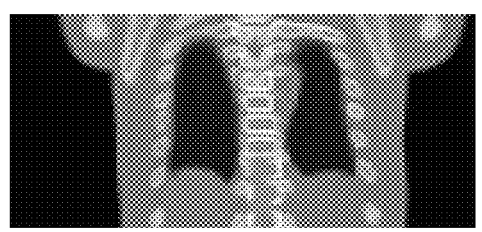
Figure 7:
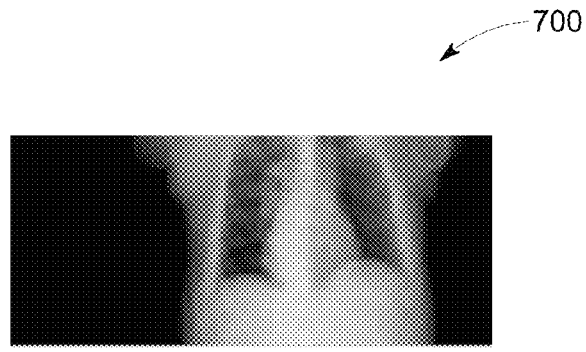
FIG. 7 illustrates an exemplary image that depicts a plurality of the true attenuation factors.

Particularly, FIG. 3 depicts a transaxial slice 300 of a true emission image, whereas FIG. 4 depicts a coronal slice 400 of the true emission image corresponding to a target volume. Further, FIGS. 5 and 6 depict transaxial and coronal slices 500 and 600, respectively, corresponding to a true attenuation map. In the exemplary implementation, the true emission image and the true attenuation map depicted in FIGS. 3-6 are used to generate simulated PET emission data such as the emission scan data that is acquired and received in step 202. Moreover, FIG. 7 depicts an exemplary image 700 that depicts a plurality of the true attenuation factors.

Figure 8:
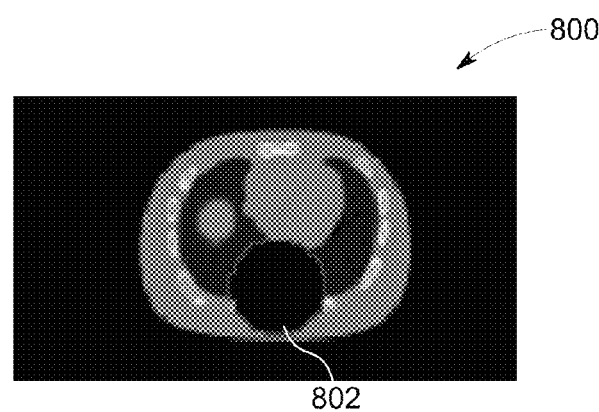
FIGS. 8 and 9 illustrate transaxial and coronal slices of an preliminary attenuation map determined from the MRI data, respectively.
Figure 9:
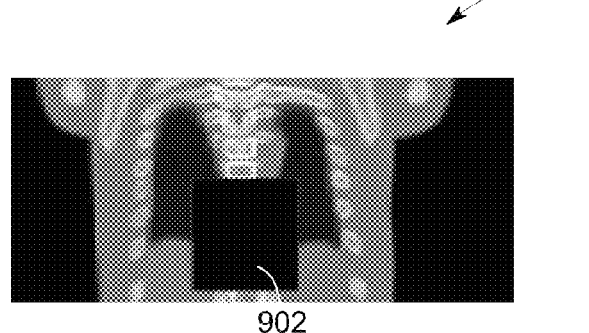
Figure 10:
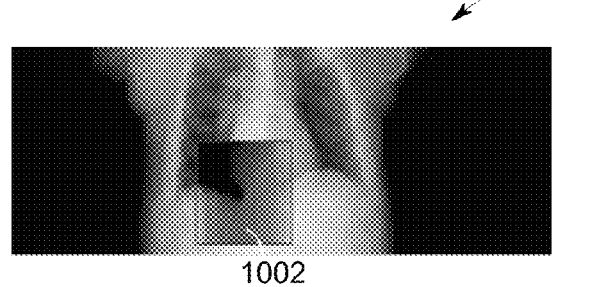
FIG. 10 illustrates an exemplary image that depicts initial attenuation factors.

Further, FIGS. 8 and 9 depict transaxial and coronal slices 800 and 900 of a preliminary attenuation map, such as the map determined at step 210, from the MRI data that is acquired at step 202 and reconstructed at step 204, respectively. As shown in FIGS. 8-9, the transaxial and coronal slices 800 and 900 include ambiguous image-regions 802 and 902, respectively, that are identified at step 206. The ambiguous image-regions 802 and 902 correspond to regions where image-space certainty value is zero as determined at step 208 and the depicted attenuation coefficient is incorrect. Similarly, FIG. 10 depicts an image 1000 that depicts initial attenuation factors, such as the attenuation factors calculated at step 212 using the preliminary attenuation map. Additionally, FIG. 10 depicts ambiguous projection-regions 1002 where the projection-space certainty value is zero, for example, as determined at step 214.

Figure 11:
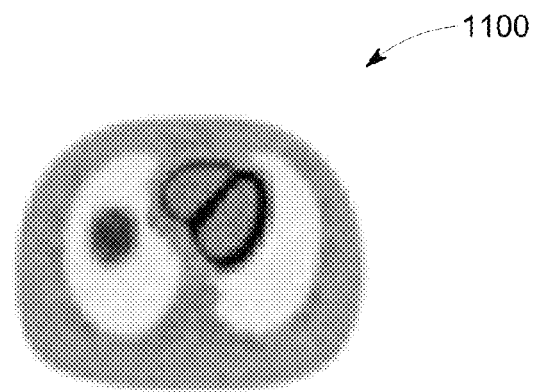
FIGS. 11 and 12 illustrate transaxial and coronal slices, respectively, of an emission image that correspond to reference reconstructions of the target volume using the true attenuation map as shown in FIGS. 5 and 6.
Figure 12:
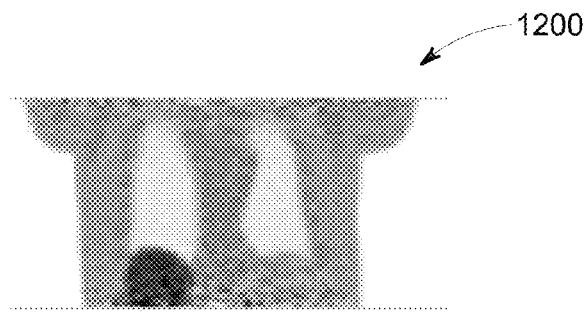
Figure 13:
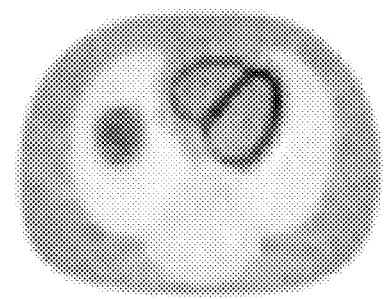
FIGS. 13 and 14 illustrate transaxial and coronal slices, respectively, of an emission image reconstructed from noisy emission scan data using the preliminary attenuation map as shown in FIGS. 8 and 9.
Figure 14:
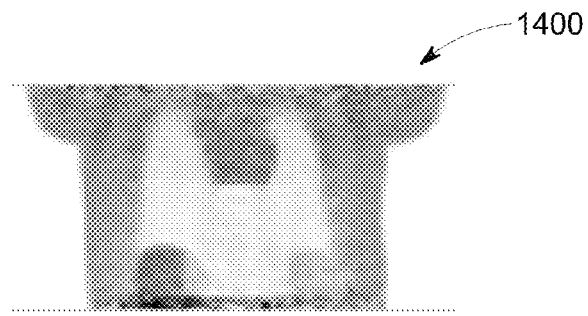

Further, FIGS. 11 and 12 depict transaxial and the coronal slices 1100 and 1200, respectively, of an emission image reconstructed from noisy TOF emission scan data using the true attenuation map, such as the attenuation map depicted in FIGS. 5 and 6, generated using OSEM. FIGS. 11-12, thus, correspond to reference reconstructions of the target volume. Additionally, FIGS. 13-14 depict transaxial and coronal slices 1300 and 1400, respectively, of an emission image reconstructed from the noisy TOF emission scan data using the preliminary attenuation map as shown in FIGS. 8 and 9. A comparison of FIGS. 13-14 and 11-12 shows a mismatch in the visualization of the target volume. Particularly, the comparison indicates that FIGS. 13-14 include image artifacts caused due to incorrect attenuation coefficients corresponding to regions 802 and 902.

Figure 15:
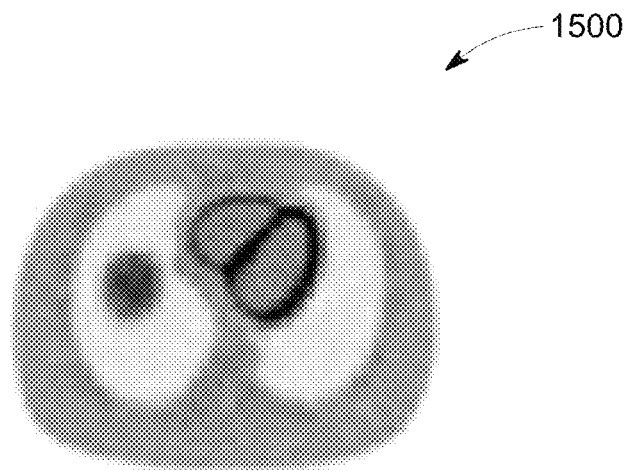
FIGS. 15 and 16 illustrate transaxial and coronal slices, respectively, of an emission image reconstructed using an embodiment of the present method described with reference to FIG. 2.
Figure 16:
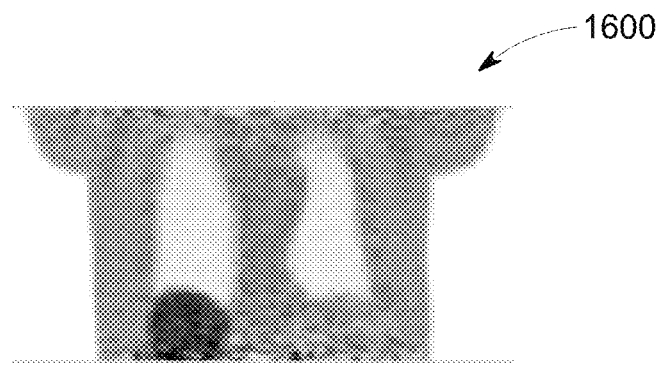
Figure 17:
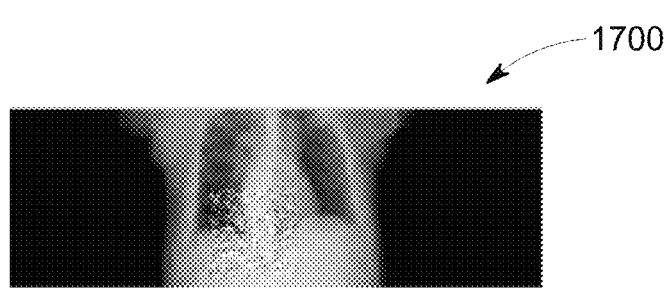
FIG. 17 illustrates the final updated attenuation factors obtained using the method described with reference to FIG. 2.

Further, FIGS. 15 and 16 depict transaxial and coronal slices 1500 and 1600, respectively, of an emission image reconstructed using an embodiment of the present method described with reference to FIG. 2. As evident from the depictions of FIGS. 15 and 16, the image artifacts depicted in FIGS. 13-14 are not observed in FIGS. 15-16. In particular, the FIGS. 15-16 appear similar to the reference reconstructions of the target volume depicted in FIGS. 11-12, thereby indicating accuracy of the attenuation factors determined using the present method. Further, FIG. 17 depicts the final and/or updated attenuation factors obtained using the method described with reference to FIG. 2.

Embodiments of the present systems and methods, thus, allow simultaneous estimation of the PET emission images and PET attenuation in the sinogram space based on PET data and MRI data. Particularly, embodiments described herein provide an improved imaging workflow that combines information from both PET and MRI scans to alleviate the challenges in attenuation correction and/or image reconstruction using only PET or only MRI data. Particularly, the present systems and methods allow for accurate identification of conventionally ambiguous image-regions such as those including bone, metal, air, lungs, truncated regions, and/or regions imaged with insufficient quality.

Moreover, estimating a subset of attenuation factors in sinogram space provides greater computational efficiency and robustness to inaccurate MR information resulting from erroneous segmentation or unavailable information. The present systems and methods, thus, allow for accurate quantitation for PET/MRI data by accurate attenuation correction and PET/MRI image reconstruction. Although the present description is drawn to PET imaging, embodiments of the present systems and methods may also apply to SPECT imaging where SPECT emission activity and SPECT attenuation maps may be reconstructed using SPECT projection data and MR, CT, EIT, and/or optical images.

It may be noted that the foregoing examples, demonstrations, and process steps that may be performed by certain components of the present systems, for example by the system controller 104, the processing subsystem 132, and the image processing unit 138 of FIG. 1, may be implemented by suitable code on a processor-based system. To that end, the processor-based system, for example, may include a general-purpose or a special-purpose computer. It may also be noted that different implementations of the present disclosure may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of various embodiments of the present disclosure may be shown in and/or described with respect to some drawings and not in others, this is for convenience only. It is to be understood that the described features, structures, and/or characteristics may be combined and/or used interchangeably in any suitable manner in various embodiments, for example, to construct additional assemblies and imaging methods.

While only certain features of the present disclosure have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for imaging a subject, comprising:
receiving emission scan data and anatomical scan data corresponding to the target volume in the subject;
reconstructing one or more at least partial anatomical scan images using the anatomical scan data;
generating an image-space certainty map that represents a level of confidence corresponding to an attenuation coefficient for one or more selected voxels in the one or more at least partial anatomical scan images;
generating a preliminary attenuation map based on the one or more at least partial anatomical scan images;
initializing one or more of a selected set of attenuation factors in a projection-space corresponding to the emission scan data based on the preliminary attenuation map;
generating a projection-space certainty map corresponding to the emission scan data that represents a level of confidence corresponding to a value of one or more of the selected set of attenuation factors based on the image-space certainty map;
initializing an emission image corresponding to the target volume in the subject;

iteratively updating one or more of the selected set of attenuation factors and the emission image based on the emission scan data, the projection-space certainty map, the initial attenuation factors, the initial emission image, or combinations thereof; and determining a desired emission image, desired values of the attenuation factors, or a combination thereof, based on the iteratively updated attenuation factors and the iteratively updated emission image.

2. The method of claim 1, further comprising acquiring the emission scan data using an emission tomography system and the anatomical scan data using an anatomical scan system that is operatively coupled to the emission tomography system.

3. The method of claim 1, wherein the emission scan data comprises positron emission tomography (PET) emission scan data, time-of-flight (TOF) PET emission scan data, single photon emission computed tomography (SPECT) emission scan data, or combinations thereof, and wherein the anatomical scan data comprises magnetic resonance (MR) imaging scan data, X-ray computed tomography (CT) scan data, X-ray data, optical data, electrical impedance tomography (EIT) data, ultrasound scan data, or combinations thereof.

4. The method of claim 1, wherein the one or more at least partial anatomical scan images comprise one or more MR images, the one or more MR images comprising fat and water images, in-phase and out-of-phase images, a proton density weighted image, an ultrashort echo time (UTE) image, a zero echo time (ZTE) image, a localizer scan image, an image determined on a gapped 3D grid, or combinations thereof.

5. The method of claim 1, wherein generating the preliminary attenuation map comprises:
segmenting the one or more at least partial anatomical scan images into a plurality of regions and assigning selected attenuation coefficients to the plurality of regions;
correlating the one or more at least partial anatomical scan images to corresponding attenuation maps using one or more mathematical transformations, atlas-based image registration, template-based image registration, or combinations thereof.

6. The method of claim 1, wherein initializing the attenuation factors comprises calculating a forward-projection of the preliminary attenuation map.

7. The method of claim 1, wherein generating the image-space certainty map comprises:
identifying one or more distinctive image-regions, and one or more ambiguous image-regions in the one or more at least partial anatomical scan images;
determining a level of confidence corresponding to an attenuation coefficient for each voxel in the one or more distinctive image-regions, the one or more ambiguous image-regions, or combinations thereof; and
generating the image-space certainty map based on the determined confidence levels.

8. The method of claim 7, wherein identifying the one or more distinctive image-regions, and the one or more ambiguous image-regions comprises segmenting the one or more at least partial anatomical scan images using thresholding, a partial differential equation, an atlas-based or template-based registration, a multi-scale model, machine learning, region growing, an active contour model, or combinations thereof.

9. The method of claim 7, wherein the one or more distinctive image-regions comprise fat, water, air, lung, or combinations thereof, and wherein the one or more ambiguous image-regions comprise one or more voxels having image intensities lesser than a selected value, one or more voxels determined using prior anatomical knowledge, or combinations thereof.

10. The method of claim 7, wherein the one or more ambiguous image-regions comprise regions that are truncated during imaging due to a small field of view corresponding to the anatomical scan imaging system, regions in the one or more at least partial anatomical scan images that are not reconstructed with desired quality, or combinations thereof.

11. The method of claim 1, wherein generating the projection-space certainty map comprises:
calculating a forward-projection of the image-space certainty map; and
generating the projection-space certainty map based on the calculated forward-projection.

12. The method of claim 1, wherein iteratively updating the one or more selected attenuation factors and the emission image comprises selectively updating the attenuation factors corresponding to one or more ambiguous projection-regions determined by the projection-space certainty map.

13. The method of claim 1, wherein iteratively updating the one or more selected attenuation factors and the emission image comprises:
updating the initial emission image based on the initial attenuation factors, and updating the initial attenuation factors based on the updated emission image; and
alternating between updating the emission image based on the updated attenuation factors in one iteration and updating the attenuation factors based on the updated emission image in a subsequent iteration.

14. The method of claim 1, further comprising:
calculating upper bounds for one or more of the selected set of attenuation factors based on the preliminary attenuation map, the image-space certainty map, the projection-space certainty map, or combinations thereof; and
imposing one or more inequality constraints based on the upper bounds when iteratively updating one or more of the selected set of attenuation factors.

15. The method of claim 1, further comprising:
determining a parametric model to represent one or more of the selected set of attenuation factors, and one or more parameters that parameterize the parametric model;
initializing the parameters corresponding to the initialized attenuation factors; and
iteratively updating the parameters and the emission image based on the emission scan data, the projection-space certainty map, or combinations thereof.

16. The method of claim 15, wherein the parametric model comprises inverse Fourier rebinning or inverse single slice rebinning, and wherein the parameters comprise one or more attenuation factors corresponding to direct plane lines of response.

17. An imaging system for imaging a subject, comprising:
an emission tomography system configured to acquire emission scan data corresponding to the subject;
an anatomical scan system operatively coupled to the emission tomography system and configured to acquire anatomical scan data corresponding to the subject;
a processing subsystem operationally coupled to one or more of the anatomical scan system and the emission tomography system, wherein the processing subsystem is configured to:

reconstruct one or more at least partial anatomical scan images using the anatomical scan data;

generate an image-space certainty map that represents a level of confidence corresponding to an attenuation coefficient for one or more selected voxels by processing the one or more at least partial anatomical scan images;

generate a preliminary attenuation map based on the one or more at least partial anatomical scan images;

initialize one or more of a selected set of attenuation factors in a projection-space corresponding to the emission scan data based on the preliminary attenuation map;

generate a projection-space certainty map corresponding to the emission scan data that represents a level of confidence corresponding to the value of one or more of the selected set of attenuation factors based on the image-space certainty map;

initialize an emission image corresponding to the target volume in the subject;

iteratively update one or more of the selected attenuation factors and the emission image based on the emission scan data, the projection-space certainty map, the initial attenuation factors, the initial emission image, or combinations thereof; and determine a desired emission image, desired values of the attenuation factors, or a combination thereof, based on the iteratively updated attenuation factors and the iteratively updated emission image.

18. The imaging system of claim 17, wherein the emission tomography system comprises a PET scanner, a SPECT scanner, a dual head coincidence imaging system, or combinations thereof, and wherein the anatomical scan system comprises a CT scanner, a magnetic resonance imaging (MRI) system, an X-ray system, an optical tomography system, an EIT imaging system, or combinations thereof.

19. The imaging system of claim 17, wherein the imaging system is an MRI system, a PET system, a SPECT system, a CT system, an X-ray system, a PET-CT system, a PET-MRI system, a SPECT-CT system, and the SPECT-MRI system, the PET-x-ray system, SPECT-x-ray system, or combinations thereof.

20. A non-transitory computer readable medium that stores instructions executable by one or more processors to perform a method for imaging, comprising:

receiving emission scan data and anatomical scan data;

reconstructing one or more at least partial anatomical scan images using the anatomical scan data;

generating an image-space certainty map that represents a level of confidence corresponding to an attenuation coefficient for one or more selected voxels in the one or more at least partial anatomical scan images;

generating a preliminary attenuation map based on the one or more at least partial anatomical scan images;

initializing one or more of a selected set of attenuation factors in a projection-space corresponding to the emission scan data based on the preliminary attenuation map;

generating a projection-space certainty map corresponding to the emission scan data that represents a level of confidence corresponding to the value of one or more of the selected set of attenuation factors based on the image-space certainty map;

initializing an emission image corresponding to the target volume in the subject;

iteratively updating one or more of the selected set of attenuation factors and the emission image based on the emission scan data, the projection-space certainty map, the initial attenuation factors, the initial emission image, or combinations thereof; and determining a desired emission image, desired values of the attenuation factors, or a combination thereof, based on the iteratively updated attenuation factors and the iteratively updated emission image.

* * * * *